United States Patent [19]

Werbel et al.

[11] Patent Number: 4,532,240
[45] Date of Patent: Jul. 30, 1985

[54] DIAMINOPYRIMIDINES

[75] Inventors: Leslie M. Werbel; Jocelyn H. Hung, both of Ann Arbor, Mich.

[73] Assignee: Warner-Lambert Company, Morris Plains, N.J.

[21] Appl. No.: 520,653

[22] Filed: Aug. 9, 1983

Related U.S. Application Data

[63] Continuation-in-part of Ser. No. 416,404, Sep. 9, 1982, abandoned.

[51] Int. Cl.³ .................. A61K 31/505; C07D 403/04
[52] U.S. Cl. .................................... 514/252; 544/295; 544/313
[58] Field of Search .................. 544/295; 424/250

[56] References Cited

U.S. PATENT DOCUMENTS

| | | | |
|---|---|---|---|
| 2,562,036 | 7/1951 | Halquist et al. | 544/295 |
| 2,748,125 | 5/1956 | Hofmann | 544/295 |
| 3,975,384 | 8/1976 | Narr et al. | 544/295 |
| 4,166,852 | 9/1979 | Loiseau et al. | 544/295 |
| 4,351,832 | 9/1982 | Rakhit et al. | 544/295 |

OTHER PUBLICATIONS

Wu et al., "Chemical Abstracts", vol. 84, 1976, Col. 17428c.

Primary Examiner—Richard L. Raymond
Assistant Examiner—James H. Turnipseed
Attorney, Agent, or Firm—Jerry F. Janssen

[57] ABSTRACT

Substituted-phenyl derivatives of 5-(1,4-piperazinyl)-2,4-pyrimidinediamine are effective as antibacterial and antitumor agents. Methods of preparing such compounds, pharmaceutical compositions based thereon, and a method of treating bacterial infections in a mammal in need of such treatment are disclosed.

32 Claims, No Drawings

DIAMINOPYRIMIDINES

CROSS REFERENCE TO RELATED APPLICATIONS

This application is a continuation-in-part of copending application Ser. No. 416,404 filed Sept. 9, 1982 now abandoned.

BACKGROUND OF THE INVENTION

This invention relates to diaminopyrimidine compounds having antibacterial and antitumor properties. More particularly, this invention is concerned with certain substituted-phenyl derivatives of 5-(1,4-piperazinyl)-2,4-diaminopyrimidine, with methods for producing these compounds, with pharmaceutical compositions including these compounds, and with a method employing these pharmaceutical compositions for the treatment of bacterial infections in a mammal.

SUMMARY OF THE INVENTION

In its broadest chemical compound aspect, the present invention is a compound having the structural formula

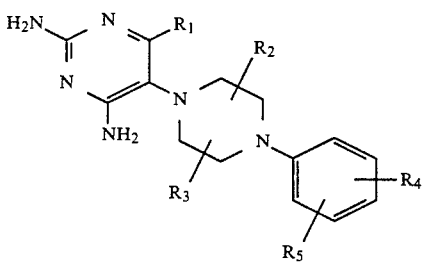

I where
A. $R_1$ is hydrogen or alkyl of from one to six carbon atoms;
B. $R_2$ and $R_3$ are independently hydrogen or methyl;
C. $R_4$ and $R_5$ are independently:
(1) hydrogen;
(2) halogen;
(3) nitro;
(4) cyano;
(5) trifluoromethyl;
(6) hydroxyl;
(7) alkyl of from one to six carbon atoms;
(8) alkoxyl of from one to six carbon atoms;
(9) alkanoyl of from one to six carbon atoms;
(10) —$NR_6R_7$, where $R_6$ and $R_7$ are independently
  (a) hydrogen,
  (b) alkyl of from one to six carbon atoms,
  (c) alkanoyl of from one to six carbon atoms;
(11) —$COOR_8$ where $R_8$ is
  (a) hydrogen,
  (b) a pharmaceutically acceptable metal cation,
  (c) a pharmaceutically acceptable amine cation,
  (d) alkyl of from one to six carbon atoms;
(12) —$CONR_9R_{10}$ where $R_9$ and $R_{10}$ are independently
  (a) hydrogen,
  (b) alkyl of from one to six carbon atoms,
  (c) alkyl of from one to six carbon atoms, substituted with one or two carboxyl groups,
(d) alkyl of from one to six carbon atoms, substituted with one or two carboxyl groups and one —OH, —SH, or —$NH_2$ group,
(e) alkyl of from one to six carbon atoms, substituted with one or two carboalkoxy groups of from one to six carbon atoms,
(f) alkyl of from one to six carbon atoms, substituted with one or two carboalkoxy groups of from one to six carbon atoms and one —OH, —SH, or —$NH_2$ group;
(13)

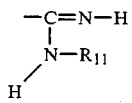

where $R_{11}$ is hydrogen, or alkyl of from one to six carbon atoms; or
(14) —$SO_2R_{12}$ where $R_{12}$ is
  (a) hydroxyl,
  (b) alkyl of from one to six carbon atoms,
  (c) alkoxy of from one to six carbon atoms, or
  (d) —$NR_{13}R_{14}$ where $R_{13}$ and $R_{14}$ are independently hydrogen or alkyl of from one to six carbon atoms;

and the pharmaceutically acceptable salts thereof.

In a first subgeneric chemical compound aspect, the present invention is a compound having structural formula I wherein $R_4$ and $R_5$ are independently selected from
A. nitro;
B. cyano;
C. trifluoromethyl;
D. alkanoyl of from one to six carbon atoms;
E. —$COOR_8$ where $R_8$ is
  (1) hydrogen,
  (2) a pharmaceutically acceptable metal cation,
  (3) a pharmaceutically acceptable amine cation, or
  (4) alkyl of from one to six carbon atoms;
F. —$CONR_9R_{10}$ where $R_9$ and $R_{10}$ are independently
  (1) hydrogen,
  (2) alkyl of from one to six carbon atoms,
  (3) alkyl of from one to six carbon atoms, substituted with one or two carboxyl groups,
  (4) alkyl of from one to six carbon atoms, substituted with one or two carboxyl groups and one —OH, —SH, or —$NH_2$ group,
  (5) alkyl of from one to six carbon atoms, substituted with one or two carboalkoxy groups of from one to six carbon atoms,
  (6) alkyl of from one to six carbon atoms, substituted with one or two carboalkoxy group of from one to six carbon atoms and one —OH, —SH, or —$NH_2$ group;
G.

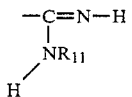

where $R_{11}$ is hydrogen or alkyl of from one to six carbon atoms; or
H. —$SO_2R_{12}$ where $R_{12}$ is
(1) hydroxyl,
(2) alkyl of from one to six carbon atoms, (3) alkoxy of from one to six carbon atoms, or
(4) —NR$_{13}$R$_{14}$ where R$_{13}$ and R$_{14}$ are independently hydrogen or alkyl of from one to six carbon atoms;
and the pharmaceutically acceptable salts thereof.

In a second subgeneric chemical compound aspect, the present invention is a compound having structural formula I wherein R$_4$ and R$_5$ are independently selected from
A. hydrogen;
B. halogen;
C. hydroxyl;
D. alkyl of from one to six carbon atoms;
E. alkoxyl of from one to six carbon atoms; or
F. —NR$_6$R$_7$, where R$_6$ and R$_7$ are independently
(1) hydrogen,
(2) alkyl of from one to six carbon atoms,
(3) alkanoyl of from one to six carbon atoms;
and the pharmaceutically acceptable salts thereof.

In a first specific chemical compound aspect, the present invention is a compound having the name 4-[4-(2,4-diamino-6-methyl-5-pyrimidinyl)-1-piperazinyl]-benzoic acid and the pharmaceutically acceptable salts thereof.

In a second specific chemical compound aspect, the present invention is a compound having the name 4-[4-(2,4-diamino-6-methyl-5-pyrimidinyl)-1-piperazinyl]-benzoic acid ethyl ester and the pharmaceutically acceptable salts thereof.

In a third specific chemical compound aspect, the present invention is a compound having the name 5-[4-(4-cyanophenyl)-1-piperazinyl]-6-methyl-2,4-pyrimidinediamine and the pharmaceutically acceptable salts thereof.

In a fourth specific chemical compound aspect, the present invention is a compound having the name N-[4-[4-(2,4-diamino-6-methyl-5-pyrimidinyl)-1-piperazinyl]-benzoyl]-L-glutamic acid and the pharmaceutically acceptable salts thereof.

In a fifth specific chemical compound aspect, the present invention is a compound having the name N-[4-[4-(2,4-diamino-6-methyl-5-pyrimidinyl)-1-piperazinyl]-benzoyl]-L-glutamic acid diethyl ester and the pharmaceutically acceptable salts thereof.

In a sixth specific chemical compound aspect, the present invention is a compound having the name 6-methyl-5-[4-(4-nitrophenyl)-1-piperazinyl]-2,4-pyrimidinediamine and the pharmaceutically acceptable salts thereof.

In a seventh specific chemical compound aspect, the present invention is a compound having the name 5-[4-(4-acetylphenyl)-1-piperazinyl]-6-methyl-2,4-pyrimidinediamine and the pharmaceutically acceptable salts thereof.

In an eighth specific chemical compound aspect, the present invention is a compound having the name 4-[4-(2,4-diamino-6-methyl-pyrimidinyl)-1-piperazinyl]-N-methyl benzamide and the pharmaceutically acceptable salts thereof.

In a ninth specific chemical compound aspect, the present invention is a compound having the name N-[4-[4-(2,4-diamino-6-methyl-5-pyrimidinyl)-1-piperazinyl]-benzoyl]glycine and the pharmaceutically acceptable salts thereof.

In a tenth specific chemical compound aspect, the present invention is a compound having the name N-[4-[4-(2,4-diamino-6-methyl-5-pyrimidinyl)-1-piperazinyl]-benzoyl]glycine methyl ester and the pharmaceutically acceptable salts thereof.

In an eleventh specific chemical compound aspect, the present invention is a compound having the name 6-methyl-5-[4-[4-(methylsulfonyl)phenyl]-1-piperazinyl]-2,4-pyrimidinediamine and the pharmaceutically acceptable salts thereof.

In a twelfth specific chemical compound aspect, the present invention is a compound having the name 5-[4-(4-cyanophenyl)-1-piperazinyl]-6-ethyl-2,4-pyrimidinediamine and the pharmaceutically acceptable salts thereof.

In a thirteenth specific chemical compound aspect, the present invention is a compound having the name 4-[4-(2,4-diamino-6-ethyl-5-pyrimidinyl)-1-piperazinyl]-benzoic acid and the pharmaceutically acceptable salts thereof.

In a fourteenth specific chemical compound aspect, the present invention is a compound having the name N-[4-[4-(2,4-diamino-6-ethyl-5-pyrimidinyl)-1-piperazinyl]benzoyl]-L-glutamic acid and the pharmaceutically acceptable salts thereof.

In a fifteenth specific chemical compound aspect, the present invention is a compound having the name N-[4-[4-(2,4-diamino-6-ethyl-5-pyrimidinyl)-1-piperazinyl]-benzoyl]-L-glutamic acid diethyl ester, and the pharmaceutically acceptable salts thereof.

In a sixteenth specific chemical compound aspect, the present invention is a compound having the name 5-[4-(4-cyanophenyl)-1-piperazinyl]-6-propyl-2,4-pyrimidinediamine and the pharmaceutically acceptable salts thereof.

In a seventeenth specific chemical compound aspect, the present invention is a compound having the name 4-[4-(2,4-diamino-6-propyl-5-pyrimidinyl)-1-piperazinyl]benzoic acid and the pharmaceutically acceptable salts thereof.

In an eighteenth specific chemical compound aspect, the present invention is a compound having the name N-[4-[4-(2,4-diamino-6-propyl-5-pyrimidinyl)-1-piperazinyl]benzoyl]-L-glutamic acid and the pharmaceutically acceptable salts thereof.

In a nineteenth specific chemical compound aspect, the present invention is a compound having the name N-[4-[4-(2,4-diamino-6-propyl-5-pyrimidinyl)-1-piperazinyl]benzoyl]-L-glutamic acid diethyl ester and the pharmaceutically acceptable salts thereof.

In a twentieth specific chemical compound aspect, the present invention is a compound having the name 4-[4-(2,4-diamino-6-propyl-5-pyrimidinyl)-1-piperazinyl]benzoic acid ethyl ester and the pharmaceutically acceptable salts thereof.

In a twenty-first specific chemical compound aspect, the present invention is a compound having name 6-methyl-5-(4-phenyl-1-piperazinyl)-2,4-6-pyrimidinediamine, hydrochloride and the pharmaceutically acceptable salts thereof.

In a twenty-second specific chemical compound aspect, the present invention is a compound having the name 5-[4-(4-chlorophenyl)-1-piperazinyl]-6-methyl-2,4-pyrimidinediamine and the pharmaceutically acceptable salts thereof.

In a twenty-third specific chemical compound aspect, the present invention is a compound having the name 5-[4-(4-aminophenyl-1-piperazinyl]-6-methyl-2,4-pyrimidinediamine and the pharmaceutically acceptable salts thereof.

In a twenty-fourth specific chemical compound aspect, the present invention is a compound having the name N-[4-[4-(2,4-Diamino-6-methyl-5-pyrimidinyl)-1- piperazinyl]benzoyl]-glycine and the pharmaceutically acceptable salts thereof.

In a twenty-fifth specific chemical compound aspect, the present invention is a compound having the name 4-[4-(2,4-Diamino-6-methyl-5-pyrimidinyl)-1-piperazinyl]-N,N-dimethylbenzenesulfonamide and the pharmaceutically acceptable salts thereof.

In a twenty-sixth specific chemical compound aspect, the present invention is a compound having the name 6-Methyl-5-[4-[4-(trifluoromethyl)phenyl]-1-piperazinyl]-2,4-pyrimidinediamine and the pharmaceutically acceptable salts thereof.

In its pharmaceutical composition aspect, the present invention is a compound having structural formula I as defined above in combination with a pharmaceutically acceptable carrier.

In its pharmaceutical method aspect, the present invention is a method for treating bacterial infections in a mammal in need of such treatment by administering an effective amount of a pharmaceutical composition comprising a compound having structural formula I as defined above in combination with a pharmaceutically acceptable carrier.

DETAILED DESCRIPTION

Compounds of the present invention are made by either of the two following methods.

In a first alternative method, detailed by Reaction Scheme I, a compound of structural formula II is reacted with an appropriately substituted fluorophenyl compound of structural formula III to produce compounds of the present invention. Compound II is condensed with the appropriately substituted fluorophenyl compound by reaction in polar organic solvents such as dimethylsulfoxide in the presence of a base such as potassium carbonate. In structural formulas I, II, and III below, $R_1$, $R_2$, $R_3$, $R_4$, and $R_5$ are as defined above.

analog. Condensation of the 5-bromouracil derivative with 1-benzylpiperazine is conducted in the presence of potassium fluoride, preferably at temperatures of between 100° C. to 150° C. for periods ranging between about 48–72 hours.

The resulting piperazine-substituted uracil is chlorinated by reaction with phosphorus oxychloride in the presence of a base such as N,N-dimethylaniline under reflux for a period of from about 2–10 hours. The chlorine substituents are replaced by amine groups, preferably by treatment with ammonia in ethanol at temperatures of between 130° C.–170° C. for periods of between about 12–18 hours.

The benzyl blocking group is removed from the piperazine moiety by hydrogenolysis over palladium/-charcoal catalyst in acetic acid to produce compounds having structural formula II.

Compounds of structural formula II are believed by the applicants to comprise a novel class of compounds serving as intermediates in the formation of the active antibacterial compounds of this invention. Thus, compounds of structure II where $R_1$ is hydrogen or alkyl of from one to six carbon atoms, and $R_2$ and $R_3$ are independently hydrogen or methyl are also contemplated as falling within the scope of the present invention.

The appropriately substituted fluorophenyl compounds of structural formula III are prepared by methods well known to practitioners of the organic chemical arts.

REACTION SCHEME I

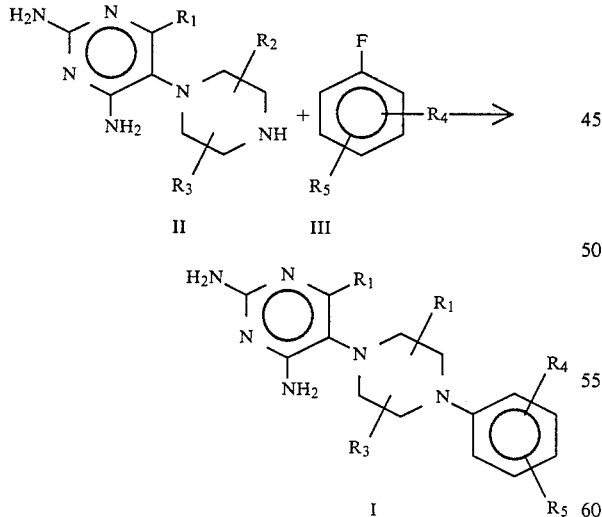

Compounds of structural formula II may be prepared by methods detailed in Reaction Scheme II. In the structural formulas given below, $R_1$, $R_2$, $R_3$, $R_4$, and $R_5$ are as defined above.

Uracil or a 6-lower-alkyl-substituted-uracil is brominated in acetic acid at a temperature ranging from ambient to 50° C. for 15–20 hours to provide the 5-bromo-

REACTION SCHEME II

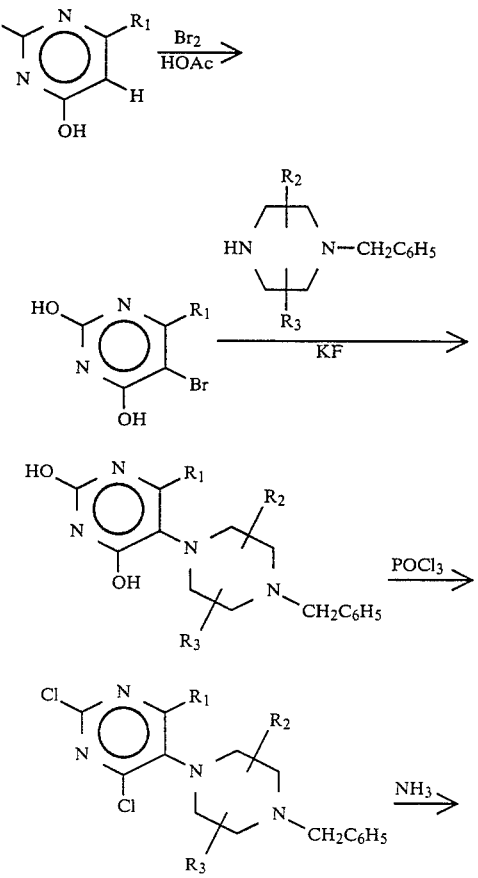

-continued
REACTION SCHEME II

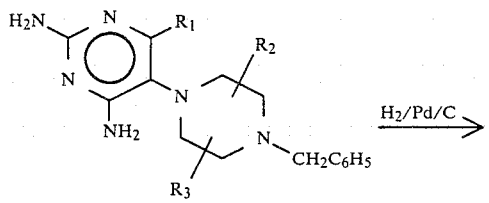

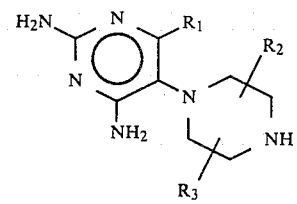

II

In the particular case where compound III is a cyano- or dicyanofluorobenzene, the cyano group or groups may be converted to compounds in accordance with the present invention in which $R_4$ and $R_5$ are carboxyl, carboxylic acid salt, and carboalkoxy (ester group) by acidic hydrolysis of the cyano group to the carboxylic acid group followed, if desired, by salt formation with a pharmaceutically acceptable metal or amine cation, or esterification with an alcohol.

Alternatively, the carboxylic acid is converted to the amide or aminoacid amide by reaction with the desired amine or aminoacid by methods well known in the organic chemical art.

In an alternative method for preparing compounds of the present invention, detailed by Reaction Scheme III, 5-bromouracil or a lower alkyl-substituted-5-bromouracil (IV) is reacted with a phenyl-substituted derivative of 1,4-piperazine of structural formula V to produce compounds of structural formula VI. Compounds of formula VI are subsequently converted to compounds in accordance with the present invention by halogenation and amination. In the structural formulas given below, $R_1$, $R_2$, $R_3$, $R_4$, and $R_5$ are as defined above.

REACTION SCHEME III

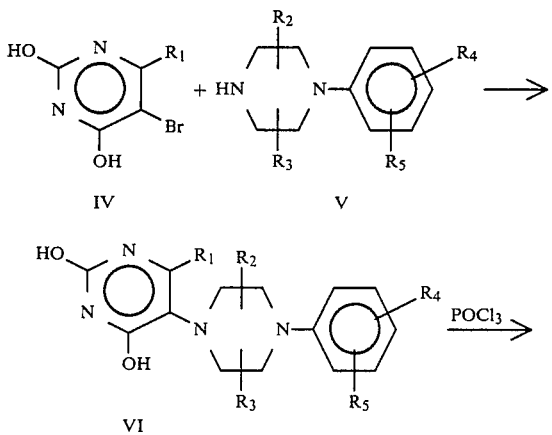

-continued
REACTION SCHEME III

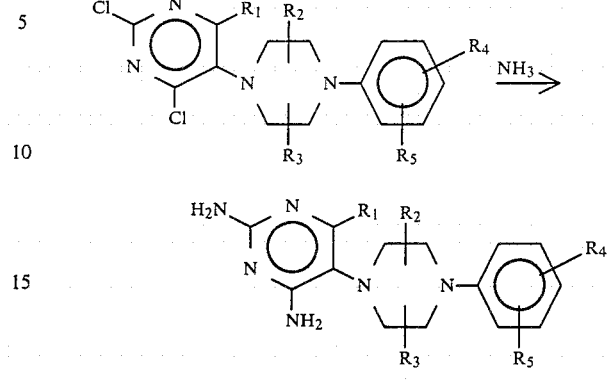

I

By the term "alkyl group" as used throughout this specification and claims, unless otherwise specified in a particular instance, is meant both straight carbon chain and branched carbon chain groups. By the term "alkoxy" or "alkoxy" group is meant an alkyl group as previously defined, attached to the parent molecule through a single oxygen atom. Alkoxyl groups can be thought of as derived from an alcohol by removal of the alcoholic hydrogen atom. Such groups include, for example, methoxyl (—OCH$_3$), ethoxyl (—OCH$_2$CH$_3$), and the like. By the term "alkanoyl" is meant an alkyl group as previously defined, attached to the parent molecule through a carbonyl group (i.e.,

Alkanoyl groups can be thought of as derived from an aldehyde by removal of the aldehydic hydrogen atom. Such groups include, for example, formyl, acetyl, propionyl, etc.

By the term "carboalkoxy" or "carboalkoxyl" as used herein is meant the carboxyl group of an organic acid, esterified with a lower alcohol. Such groups include, for example, carbomethoxy, carboethoxy, etc.

The compounds of the present invention, where $R_4$ and/or $R_5$ are acidic functions, form pharmaceutically acceptable salts with organic and inorganic bases. Examples of suitable inorganic bases are ammonium hydroxide, sodium hydroxide, potassium hydroxide, sodium carbonate, calcium carbonate, sodium bicarbonate, and the like. Pharmaceutically acceptable salts are also formed with amine cations derived from organic nitrogenous bases strong enough to form cations.

The pharmaceutically acceptable salts of the acid are prepared by, for example, suspending the acid in water and adjusting the pH with the pharmaceutically acceptable base, or by reacting the compound with one equivalent of the pharmaceutically acceptable base in a solvent and removing the solvent under reduced pressure.

The term, pharmaceutically acceptable metal cation contemplates the positively charged ions derived from such metals as sodium, potassium, calcium, magnesium, aluminum, zinc, iron, and the like. The salts are prepared by contacting the free form of the compound with an equivalent amount of the desired base in the conventional manner. The free forms may be regenerated by treating the salt form with an acid. For example dilute aqueous acid solutions may be utilized to regenerate the free form from a respective salt. Dilute aqueous hydrochloric acid is suitable for this purpose. The free forms differ from their respective salt forms somewhat in certain physical properties such as solubility in polar solvents, but the salts are otherwise equivalent to their respective free base forms for purposes of the invention.

The term pharmaceutically acceptable amine cation contemplates the positively charged ammonium ion and analogous ions derived from organic nitrogenous bases strong enough to form such cations. Bases useful for the purpose of forming pharmacologically acceptable non-toxic addition salts of such compounds containing free carboxyl groups form a class whose limits are readily understood by those skilled in the art. Merely for illustration, they can be said to comprise, in cationic form, those of the formula:

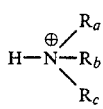

wherein $R_a$, $R_b$, and $R_c$, independently, are hydrogen, alkyl of from about one to about six carbon atoms, cycloalkyl of from about three to about six carbon atoms, aryl of about six carbon atoms, aralkyl of from about 7 to about 11 carbon atoms, hydroxyalkyl of from about 2 to about 4 carbon atoms, or monoarylhydroxyalkyl of from about 8 to about 15 carbon atoms, or, when taken together with the nitrogen atom to which they are attached, any two of $R_a$, $R_b$, and $R_c$ may form part of a 5- to 6-membered heterocyclic ring containing carbon, hydrogen, oxygen, or nitrogen, said heterocyclic rings and said aryl groups being unsubstituted or mono- or dialkyl substituted said alkyl groups containing from about one to about six carbon atoms.

The compounds of the invention form pharmaceutically acceltable salts with both organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic, isethionic, lactic, gluconic, glucuronic, sulfamic, benzoic, tartaric, pamoic, and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, with pharmaceutically acceptable solvents such as water, ethanol and the like are equivalent to the unsolvated forms for purposes of the invention.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Topical preparations include dusting powders, creams, lotions, gels, and sprays. These various topical preparations may be formulated by well known procedures. See for example Remington's Pharmaceutical Sciences, Chapter 43, 14th ed. 1970, Mack Publishing Co., Easton Pa. 18042, USA.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged form.

The quantity of active compound in a unit dose of preparation may be varied or adjusted from 50 mg to 500 mg according to the particular application and the potency of the active ingredient.

In therapeutic use as antibiotic and antifungal agents the compounds utilized in the pharmaceutical method of this invention are administered at the initial dosage of about 0.1 mg to about 50 mg per kilogram. A dose range of about 0.5 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitation inherent in the art of compounding such an active material for the treatment of disease in living subjects having a diseased condition in which bodily health is impaired as herein disclosed in deta 1.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 500 mg, with from about 0.5 to about 250 mg being preferred. Expressed in proportions, the active compound is generally present in from about 0.1 to about 500 mg/ml of carrier. In the case of compositions containing supplementary active ingredients, the dosages are determined by reference to the usual dose and the manner of administration of the said ingredients. The daily parenteral doses for mammalian subjects to be treated ranges from 0.1 mg/kg to 100 mg/kg. The preferred daily dosage range is 0.3 mg/kg to 10 mg/kg.

The following nonlimiting examples illustrate the inventors' preferred methods for preparing the compounds of the invention.

The compounds of the invention display antimicrobial and antitumor activity when assayed by standard test procedures.

In vitro Antitumor Screening of Compounds of the Present Invention on L1210 Murine Leukemia Cell Lines L1210 cells, a murine leukemia cell line, were grown in RPMI 1640 supplemented with 5% fetal bovine serum and gentamicin (50 $\mu$g/ml).

Drug dilutions were prepared in the appropriate solvent and 20 $\mu$l of each dilution were added to 24-well Linbro tissue culture plates, followed by the addition of M 2.0 ml of cell suspension containing $3 \times 10^4$ cells per ml. Solvent and medium controls were included in each test. After incubation at 37° C. for three days in 5% $CO_2$, the contents of each well were removed and the cells counted in a ZBI Coulter counter. Percent growth was calculated relative to the controls and the levels of drug activity were expressed as $ID_{50}$ in moles per liter using probit paper.

The results of these tests are presented in Table I.

TABLE I

In Vitro Activity of 2,4-Pyrimidinediamines Against L1210 Leukemia in Mice $$H_2N-\underset{NH_2}{\underset{N}{\bigcirc}}\underset{R_3}{\overset{R_1}{\underset{N}{\bigvee}}}N-\underset{R_3}{\overset{R_2}{\bigvee}}N-\underset{R_5}{\overset{R_4}{\bigcirc}}$$

| $R_1$ | $R_2$ | $R_3$ | $R_4$ | $R_5$ | L1210 Leukemia in vitro $ID_{50}$ Molar |
|---|---|---|---|---|---|
| $CH_3$ | H | H | 4-H | H | $1.5 \times 10^{-7}$ |
| $CH_3$ | H | H | 4-Cl | H | $2.8 \times 10^{-8}$ |
| $CH_3$ | H | H | $4\text{-}NH_2$ | H | $8.0 \times 10^{-8}$ |
| $CH_3$ | H | H | 4-CN | H | $1.5 \times 10^{-6}$ |
| $CH_3$ | H | H | $4\text{-}CO_2C_2H_5$ | H | $5 \times 10^{-9}$ |
| $CH_3$ | H | H | $4\text{-}COCH_3$ | H | $5 \times 10^{-9}$ |
| $CH_3$ | H | H | $4\text{-}SO_2CH_3$ | H | $5.6 \times 10^{-9}$ |
| $CH_3$ | H | H | $4\text{-}NO_2$ | H | $1.5 \times 10^{-8}$ |
| $CH_3$ | H | H | $4\text{-}CONHCH_3$ | H | $2.5 \times 10^{-9}$ |
| $CH_3$ | H | H | $4\text{-}CONHCH_2COOCH_3$ | H | $1.7 \times 10^{-8}$ |
| $C_2H_5$ | H | H | 4-CN | H | $7.7 \times 10^{-9}$ |
| $C_2H_5$ | H | H | $4\text{-}CO_2H$ | H | $1.0 \times 10^{-8}$ |
| $C_2H_5$ | H | H | $4\text{-}CONH\text{—}\underset{COOC_2H_5}{CH(CH_2)_2COOC_2H_5}$ | H | $3.2 \times 10^{-9}$ |
| $C_2H_5$ | H | H | $4\text{-}CONH\text{—}\underset{COOH}{CH(CH_2)_2COOH}$ | H | $2.0 \times 10^{-6}$ |
| $C_3H_7$ | H | H | 4-CN | H | $8.9 \times 10^{-9}$ |
| $C_3H_7$ | H | H | 4-COOH | H | $4.3 \times 10^{-8}$ |
| $C_3H_7$ | H | H | $4\text{-}COOC_2H_5$ | H | $9.3 \times 10^{-9}$ |
| $C_3H_7$ | H | H | $4\text{-}CONH\underset{COOC_2H_5}{CH(CH_2)_2COOC_2H_5}$ | H | |
| $C_3H_7$ | H | H | $4\text{-}CONH\underset{COOH}{CH(CH_2)_2COOH}$ | H | $7.5 \times 10^{-9}$ |

In addition to their usefulness as antileukemic agents, certain of the compounds of the invention display in vitro activity against solid tumors when tested by the following procedure.

HCT-8 (human colon adenocarcinoma) cells are trypsinized using Trypsin-EDTA. A single cell suspension is achieved by passing the cells through a 26 gauge needle with a 20 cc syringe. A cell suspension is prepared using RPMI 1640+10% FCS+50 μg/ml garamycin with a cell concentration of approximately 30,000 cells/ml. The cell suspension is dispensed in Linbro 24-well plates; 1 ml/well. The plates are incubated for approximately 48 hours at 37° C. in a 5% $CO_2$ atmosphere. At this time test compounds are added in the appropriate concentration. Five μl of the 200 μg/ml stock solution is added to each well in a primary test. Ten μl of the appropriate dilution is added to each well for a titration test. The plates are reincubated an additional 60-65 hours at 37° C. in a 5% $CO_2$ atmosphere. The test is read by lysing the cells using a mix of cationic surfactant, glacial acetic acid and sodium chloride. Two ml of the lysed cell suspension from each well is added to 8 ml of diluent. Each sample is read on the Coulter counter (ZBI model). The activity of each sample is measured as a percentage of the controls and the data is reported as $ID_{50}$, that is the molar quantity of drug required to kill 50% of the tumor cells.

Utilizing this procedure, the results presented in Table II were obtained for representative compounds of the invention.

TABLE II

In Vitro Activity of 2,4-Pyrimidinediamines Against Human Colon Adenocarcinoma $$H_2N-\underset{NH_2}{\underset{N}{\bigcirc}}\underset{R_3}{\overset{R_1}{\underset{N}{\bigvee}}}N-\underset{R_3}{\overset{R_2}{\bigvee}}N-\underset{R_5}{\overset{R_4}{\bigcirc}}$$

| $R_1$ | $R_2$ | $R_3$ | $R_4$ | $R_5$ | $ID_{50}$ Molar |
|---|---|---|---|---|---|
| $CH_3$ | H | H | 4-Cl | H | $3.5 \times 10^{-7}$ |
| $CH_3$ | H | H | 4-CN | H | $>1 \times 10^{-6}$ |
| $CH_3$ | H | H | $4\text{-}CO_2C_2H_5$ | H | $4.9 \times 10^{-8}$ |
| $CH_3$ | H | H | $4\text{-}COCH_3$ | H | $5.1 \times 10^{-7}$ |
| $CH_3$ | H | H | $4\text{-}SO_2CH_3$ | H | $6.1 \times 10^{-8}$ |
| $CH_3$ | H | H | $4\text{-}NO_2$ | H | $>1 \times 10^{-6}$ |
| $CH_3$ | H | H | $4\text{-}CONHCH_3$ | H | $6.7 \times 10^{-8}$ |
| $CH_3$ | H | H | $4\text{-}CONHCH_2COOCH_3$ | H | $8.0 \times 10^{-7}$ |
| $C_2H_5$ | H | H | 4-CN | H | $8.9 \times 10^{-8}$ |
| $C_2H_5$ | H | H | $4\text{-}CO_2H$ | H | $5.7 \times 10^{-7}$ |
| $C_2H_5$ | H | H | $4\text{-}CONH\text{—}\underset{COOC_2H_5}{CH(CH_2)_2COOC_2H_5}$ | H | $2.6 \times 10^{-8}$ |
| $C_2H_5$ | H | H | $4\text{-}CONH\text{—}\underset{COOH}{CH(CH_2)_2COOH}$ | H | $1.2 \times 10^{-7}$ |
| $C_3H_7$ | H | H | 4-CN | H | $1.2 \times 10^{-7}$ |
| $C_3H_7$ | H | H | $4\text{-}CO_2H$ | H | $2.8 \times 10^{-7}$ |
| $C_3H_7$ | H | H | $4\text{-}CO_2C_2H_5$ | H | $2.1 \times 10^{-7}$ |
| $C_3H_7$ | H | H | $CONH\text{—}\underset{COOH}{CH(CH_2)_2COOH}$ | H | $8.5 \times 10^{-8}$ |

The in vivo lymphocytic leukemia P388 test is carried out using the test system of the United States National Cancer Institute. The animals used are either male or female $CD_2F_1$ mice. There are six to seven animals per test group. The tumor transplant is by intraperitoneal injection of dilute ascitic fluid containing cells of lymphocytic leukemia P388. The test compounds are administered intraperitoneally in two single doses with a four-day interval between doses at various dose levels following tumor inoculation. The animals are weighed and survivors are recorded on a regular basis for 30 days. A ratio of survival time for treated (T)/control (C) animals is calculated. The criterion for efficacy is $T/C \times 100 > 125\%$. The positive control compound in this test is 5-fluorouracil. See *Cancer Chemotherapy Reports*, Part 3, 3, 1 (1972) for a comprehensive discussion of the protocol.

Utilizing this procedure, the results presented in Table III were obtained for representative compounds of the invention.

TABLE III

In Vivo Antileukemia Activity of 2,4-Pyrimidinediamines Against P388 Leukemia In Mice

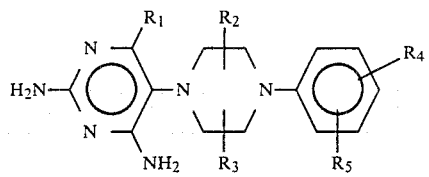

| $R_1$ | $R_2$ | $R_3$ | $R_4$ | $R_5$ | Dose (mg/kg) | P388 Leukemia in Mice T/C × 100 (survival rate after 30 days) |
|---|---|---|---|---|---|---|
| $CH_3$ | H | H | 4-CONHCH($CO_2H$)$CH_2CH_2CO_2H$ | H | 50 | 188  222 |
|  |  |  |  |  | 25 | 172  167 |
|  |  |  |  |  | 12.5 | 155  168 |
|  |  |  |  |  | 6.25 | 144  137 |
| $CH_3$ | H | H | 4-$CO_2H$ | H | 50 | 258 (3/6) |
|  |  |  |  |  | 25 | 137 |
|  |  |  |  |  | 12.5 | —  179, 227 |
|  |  |  |  |  | 6.25 | —  141, 146 |
| $CH_3$ | H | H | 4-$SO_2CH_3$ | H | 50 | 198 |
|  |  |  |  |  | 25 | 140 |
|  |  |  |  |  | 12.5 | 131 |
|  |  |  |  |  | 6.25 | 128 |
| $CH_3$ | H | H | 4-$COCH_3$ | H | 50 | 250 |
|  |  |  |  |  | 25 | 181 |
|  |  |  |  |  | 12.5 | 144 |
|  |  |  |  |  | 6.25 | 123 |
| $C_2H_5$ | H | H | 4-CN | H | 50 | 126 |
| $C_2H_5$ | H | H | 4-CONHCH$CH_2CH_2COOC_2H_5$ \| $COOC_2H_5$ | H | 50 | 258 (5/6) |
|  |  |  |  |  | 25 | 241 (2/6) |
|  |  |  |  |  | 12.5 | 183 |
|  |  |  |  |  | 6.25 | 163 |
| $C_3H_7$ | H | H | 4-$COOC_2H_5$ | H | 50 | 149 |
|  |  |  |  |  | 25 | 120 |

The compounds of the invention are new chemical substances of value as pharmacological agents for the treatment of bacterial infections in warm-blooded animals. They may also be utilized as antiseptic agents such as for use in the sterilization of laboratory glassware, etc. The antibacterial activity of representative compounds of the invention was established by the screening procedure described below.

Preparation of bacterial inocula

Vegetative bacterial isolates are maintained on agar slants or in liquid media, hereby designated as inoculum media. The cultures are transferred at regular intervals in such media. (See Table IV for the corresponding inoculum media of each culture.) The organisms are generally transferred either onto agar slants or into liquid inoculum media and incubated at 37° C. (at 28° C. with Xanthomonas sp.) overnight (18–20 hours).

The microbial cells from the overnight agar slants are then scraped off and suspended in saline solution (0.85% NaCl). The microbial concentrations are adjusted to a light transmission of 8.6% using a PerkinElmer Model 35 spectrophotometer (550 nm). For the organisms that are maintained in liquid media, one of two procedures is followed: (1) the culture suspension is first centrifuged at 5000 rpm for five minutes. The pellet is resuspended in 0.85% saline to 8.6% light transmittancy; (2) an aliquot of the culture suspension is to be added directly to the assay medium.

Isolate spore suspensions (Bacillus sp.) are maintained at 4° C. These suspensions serve as the inoculum media for assays.

Preparation of assay plates

A given molten-agar assay medium, maintained in a flask at approximately 45° C., is inoculated with 0.16–10 ml of an appropriate cell or spore suspension per 100 ml of medium. Fifty ml of the inoculated medium is poured into a Bio-Assay dish (A/S Nunc; Gibco Laboratories Catalog Number 240835) and spread evenly across the bottom, then allowed to solidify at room temperature. Each agar dish is inverted and refrigerated until used.

Disking of samples

The compounds or samples to be tested are dissolved in suitable solvents, e.g., alcohols, dimethylsulfoxide, or N,N-dimethylformamide. The samples are generally dissolved so that the final concentration of the solvent is <10%.* The compounds are tested at different concentrations: 3,000; 1,000; 500; 100; and 10 mcg/ml. Paper discs (12.7 mm diameter) saturated with a given concentration of test compound are placed onto the seeded agar dishes with a pair of forceps. (*If the compound does not stay in solution at <10% alcohol, then the full strength alcohol is used. However, the impregnated discs are air-dried before they are laid on to the seeded agar plates.)

Interpretation of results

The disked agar dishes are incubated at 37° C. (28° C. for Xanthamonas sp.) for 18–20 hours. Active compounds show a zone of inhibition around the disc. The diameter of the zone is measured in mm. The zone diameter of active compounds ranges from a minimum of 13.5 mm to as high as 60 mm. The size of the zone diameter generally reflects the activity of the compound: the larger the zone the greater the activity.

TABLE IV

| Culture | Number | Inoculum Medium | Inoculum Level ml/100 ml |
|---|---|---|---|
| Bacillus subtilis | 04555 | Spore Suspension | 0.5 |
| Branhamella catarrhalis | 03596 | T. Soy Agar | 1 |
| Streptococcus faecalis | 05045 | Folic Acid Assay Broth | 2 |
| Micrococcus luteus | 05064 | AM-07 Broth | 0.16 |
| Xanthomonas phascoli | 06002 | T. Soy Agar | 1 |

Utilizing the above described procedure, the following results, presented in Table V, were obtained for representative compounds of the invention.

TABLE V

Antimicrobial Activity of 2,4-Pyrimidinediamines

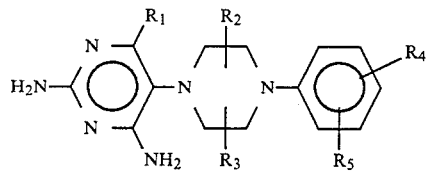

| | | | | | | Inhibition Zone diameter mm (conc.) mg/ml | | | | |
|---|---|---|---|---|---|---|---|---|---|---|
| $R_1$ | $R_2$ | $R_3$ | $R_4$ | | $R_5$ | B. subtilis | B. catarrhalis | M. faecalis | S. lutea | X. phaseoli |
| $CH_3$ | H | H | 4-CN | | H | 0 (3.0) | 0 (3.0) | 15 (0.1) | 0 (3.0) | 0 (3.0) |
| $CH_3$ | H | H | 5-COOH | | H | 15 (0.5) | 17 (0.5) | 21 (0.1) | 15 (0.1) | 0 (3.0) |
| $CH_3$ | H | H | 4-CONHCHCH$_2$CH$_2$COOH<br>                   \|<br>                   COOH | | H | 22 (0.01) | 25 (0.01) | 0 (3.0) | 0 (3.0) | 0 (3.0) |
| $CH_3$ | H | H | 4-COCH$_3$ | | H | 23 (0.1) | 24 (0.1) | 16 (0.1) | 14 (0.01) | 0 (3.0) |
| $CH_3$ | H | H | 4-SO$_2$CH$_3$ | | H | 29 (0.01) | 14 (0.5) | 18 (0.01) | 0 (3.0) | 0 (3.0) |
| $C_2H_5$ | H | H | 4-COOH | | H | 18 (0.1) | 27 (0.5) | 19 (0.01) | 16 (0.01) | 0 (3.0) |
| $C_2H_5$ | H | H | 4-CONHCHCH$_2$CH$_2$COOHC$_2$H$_5$<br>                   \|<br>                   COOC$_2$H$_5$ | | H | 19 (0.1) | 20 (0.01) | 15 (0.01) | 19 (0.01) | 3 (3.0) |
| $C_2H_5$ | H | H | 4-CONHCHCH$_2$CH$_2$COOH<br>                   \|<br>                   COOH | | H | 20 (0.1) | 14 (0.01) | 14 (0.1) | 14 (0.5) | 15 (3.0) |
| $C_3H_7$ | H | H | 4-COOH | | H | 0 (3.0) | 19 (0.5) | 15 (0.01) | 16 (0.1) | 0 (3.0) |
| $C_3H_7$ | H | H | 4-COOC$_2$H$_5$ | | H | 0 (3.0) | 15 (0.1) | 15 (0.01) | 16 (0.1) | 0 (3.0) |
| $C_3H_7$ | H | H | 4-CONHCHCH$_2$CH$_2$COOH<br>                   \|<br>                   COOH | | H | 0 (3.0) | 18 (3.0) | 16 (0.1) | 16 (1.0) | 0 (3.0) |

The following preparative examples are provided to enable one skilled in the art to practice the present invention. These examples, however, are not to be viewed as limiting the scope of the invention as it is defined by the appended claims, but to be merely illustrative thereof.

EXAMPLE 1

4-[4-(2,4-Diamino-6-methyl-5-pyrimidinyl)-1-piperazinyl]benzoic acid hydrochloride A solution of 12.10 g (0.026 mole) of 5-[4-(4-cyanophenyl)-1-piperazinyl]-6-methyl-2,4-pyrimidinediamine in 200 ml of hydrochloric acid was heated under reflux for four hours. The solution was then cooled and poured into 500 ml of ice water. The solid which formed was collected and washed with water. The solid was redissolved in 1000 ml of 1N aqueous sodium hydroxide solution and the resulting solution filtered. The pH of the filtrate was adjusted to pH 2 by the addition of 6N hydrochloric acid and the solid which precipitated was collected, washed with water and methanol, and dried in vacuo overnight at 67° C. to yield 8.38 g of the product as a white powder, mp>310° C.

5-[4-(4-Cyanophenyl)-1-piperazinyl]-6-methyl-2,4-pyrimidinediamine

A mixture of 12.5 g (0.060 mole of 6-methyl-5-(1-piperazinyl)-2,4-pyrimidinediamine, 7.27 g (0.060 mole) of 4-fluorobenzonitrile, and 8.28 g (0.060 mole) of potassium carbonate was heated at 100° C. for two hours in 100 ml of dimethylsulfoxide. The mixture was then cooled and poured into 500 ml of ice water. The solid which separated was triturated with hot dimethylsulfoxide and then dried in vacuo overnight at 67° C. to give 15.56 g of the product as a white solid, mp>310° C.

6-Methyl-5-(1-piperazinyl)-2,4-pyrimidinediamine hydrate

A solution of 43.73 g (0.147 mole) of 6-methyl-5-[4-benzyl]-1-piperazinyl]-2,4-pyrimidinediamine in 800 ml of acetic acid was hydrogenolyzed over 4 g of 20% palladium on charcoal under 3.5 atmospheres of hydrogen for 21.6 hours. The solvent was removed under vacuum and the residue was dissolved in 1000 ml of ice water and neutralized with 50% aqueous sodium hydroxide solution to a final pH of 8. The solid which separated was collected, washed with water and then a small amount of methanol. The solid was dried in vacuo overnight at 67° C. to yield 23.13 g of the product as an off-white solid. Recrystallization from acetonitrile gave 0.85 g of pure material, mp 226°–228° C.

6-Methyl-5-[4-(benzyl)-1-piperazinyl]-2,4-pyrimidinediamine 2,4-Dichloro-6-methyl-5-[4-(benzyl)-1-piperazinyl]-pyrimidine (3.40 g (0.01 mole) was dissolved in 30 ml of cold ethanol which had been previously saturated with ammonia. The solution was heated in a closed steel container at 160° C. for 16 hours. The reaction mixture was cooled and poured into 200 ml of cold 1N aqueous sodium hydroxide solution. The solid was collected, washed with water, and then recrystallized six times from ethanol to yield 0.99 g of the product as shiny beige plates, mp 209°–210° C.

2,4-Dichloro-6-methyl-5-[4-(phenylmethyl)-1-piperazinyl]-pyrimidine

A solution of 4.0 g (0.013 mole) of 6-methyl-5-[4-(phenylmethyl)-1-piperazinyl]-2,4(1H,3H)-pyrimidinedione and 1 ml of N,N-dimethylaniline in 50 ml of phosphorous oxychloride was heated under reflux for three hours. The remaining excess phosphorous oxychloride was removed under vacuum and the gummy solid which remained was poured into 200 ml of ice water containing 20 g of sodium carbonate. The solid which formed was collected, washed with water, and dried in vacuo at 60° C. to give 3.42 g of the product as a brownish solid which was used without further purification.

6-Methyl-5-[4-(phenylmethyl)-1-piperazinyl]-2,4(1H,3H)-pyrimidinedione

A mixture of 20.5 g (0.10 mole) of 5-bromo-6-methyl-2,4(1H,3H)pyrimidinedione and 10.3 g (0.11 mole) of potassium fluoride dihydrate in 130 ml of 1-benzylpiperazine was heated under reflux for 72 hours. The reaction mixture was then cooled and poured into 800 ml of ice water. The solid which formed was collected and washed with water to give 8.10 g of the product as an off-white solid. A 1.0 g portion of the crude product was recrystallized from methanol to give an off-white solid, mp 263° C.

5-Bromo-6-methyl-2,4(1H,3H)pyrimidinedione

Bromine (39.97 g, 0.25 mole) was added dropwise to a cooled mixture of 31.5 g (0.25 mole) of 6-methyl-2,4(1H,3H)pyrimidinedione in 200 ml of glacial acetic acid. The resulting mixture was stirred at ambient temperature for 16 hours and then filtered. The solid which was collected was washed with water and dried in vacuo overnight at 69° C. to give 39.9 g of the product as a white solid, mp 254° C. (dec.).

EXAMPLE 2

N-[4-[4-(2,4-Diamino-6-methyl-5-pyrimidinyl)-1-piperazinyl]benzoyl]-L-glutamic acid diethyl ester A mixture of 4.27 g (0.01137 mole) of 4-[4-(2,4-diamino-6-methyl-5-pyrimidinyl)-1-piperazinyl]benzoic acid hydrochloride, 6.12 g (0.0375 mole) of diethyl phosphorocyanidate and 7.0 ml (0.050 mole) of triethylamine in 300 ml of previously dried dimethylformamide was stirred at room temperature for five hours and then at 80° C. for five minutes. The solution was cooled to room temperature, and a solution of 3.00 g (0.0125 mole) of L-glutamic acid diethyl ester hydrochloride and 1.74 ml (0.0125 mole) of triethylamine was added. The resulting mixture was stirred for two hours at room temperature. The solvent was removed under high vacuum at 40° C. and the gummy residue partitioned between 500 ml of dichloromethane and 500 ml of 5% sodium bicarbonate solution. The organic layer was separated, washed with water and then with saturated sodium chloride solution and dried over magnesium sulfate. The dried solution was concentrated in vacuo to give a yellow solid. Recrystallization from acetonitrile gave 3.9 g of the product as a tan solid, mp 224° C. (dec.).

EXAMPLE 3

N-[4-[4-(2,4-diamino-6-methyl-5-pyrimidinyl)-1-piperazinyl]benzoyl]-L-glutamic acid A mixture of 3.00 g (0.0058 mole) of N-[4-[4-(2,4-diamino-6-methyl-5-pyrimidinyl)-1-piperazinyl]-benzoyl]-L-glutamic acid diethyl ester and 12.5 ml of 1N aqueous sodium hydroxide solution in 150 ml of methanol was stirred at room temperature for four hours. The methanol was removed under vacuum at 23° C. and the residue was dissolved in 100 ml of ice water and then neutralized by the addition of 2.5 g (0.0129 moles) of citric acid. The solid precipitate was collected, washed with water, and then triturated several times with ethanol. The remaining solid was dried overnight in vacuo at 67° C. to give 0.75 g of the product as a white powder, mp 270° C. (dec.).

EXAMPLE 4

6-Methyl-5-[4-(4-nitrophenyl)-1-piperazinyl]-2,4-pyrimidinediamine, hydrate (10:1)

A mixture of 2.08 g (0.010 mole) of 6-methyl-5-(1-piperazinyl)-2,4-pyrimidinediamine 1.69 g (0.012 mole) of p-fluoronitrobenzene and 1.38 g (0.010 mole) of potassium carbonate in 100 ml of ethanol was heated at reflux for 16 hours. Ethanol was removal in vacuo at 40° C. The solid residue was washed with 50 ml of water. Trituration with 50 ml of boiling N,N-dimethylformamide and drying in vacuo at 67° C. for 16 hours afforded 2.01 g of the product as a dull yellow solid solvated with 0.1 equivalent of water; mp>300° C.

EXAMPLE 5

5-[4-(4-acetylphenyl)-1-piperazinyl]-6-methyl-2,4-pyrimidinediamine, hydrate (100:18)

A mixture of 1.0 g (5.0 mmole) of 6-methyl-5-(1-piperazinyl)-2,4-pyrimidinediamine, 0.7 g (50 mmole) of p-fluoroacetophenone, 0.7 g (5.0 mmole) of cupric oxide, 0.7 g (5.0 mmole) of potassium carbonate in 20 ml of dimethylsulfoxide was heated under reflux at 150° C. for three hours. The reaction mixture was cooled and filtered. The solid was triturated with 200 ml of boiling N,N-dimethylformamide and filtered. The filtrate was chilled in the refrigerator for 16 hours. The crystals were collected and triturated with 20 ml of hot methanol and dried in vacuo at 78° C. for five hours to give 1.0 g of the product as an off-white solid solvated with 0.18 equivalent of water; mp>300° C.

EXAMPLE 6

4-[4-(2,4-Diamino-6-methyl-5-pyrimidinyl)-1-piperazinyl]benzoic acid, ethyl ester A mixture of 5.0 g (0.016 mole) of 5-[4-(4-cyanophenyl)-1-piperazinyl]-6-methyl-2,4-pyrimidinediamine, 30 ml of 95% ethanol and 30 ml of sulfuric acid was heated under reflux at 130° C. for four hours and cooled. The solution was poured into 400 g of ice. The solid was collected, washed first with 5N aqueous sodium carbonate solution and then with 50 ml of water. Recrystallization from N,N-dimethylformamide gave 1.72 g of the product as an off-white solid, mp 281°–285° C.

EXAMPLE 7

4-[4-(2,4-Diamino-6-methyl-5-pyrimidinyl)-1-piperazinyl]-N-methyl benzamide, hydrate (100:45)

A mixture of 2.6 g (8.0 mmole) of 4-[4-(2,4-diamino-6-methyl-5-pyrimidinyl)-1-piperazinyl]benzoic acid, 4.3 g (26.4 mmole) of diethyl phosphorocyanidate and 3.7 ml (26.4 mmole) of triethyl amine in 500 ml of N,N-dimethylformamide (dried over 4 Å molecular sieves overnight) was stirred at room temperature for five hours. Gaseous monomethylamine was passed into the suspension for one hour. The suspension initially became a clear solution and then a precipitate formed. The solvent was removed under high vacuum (0.1 mm, dry ice-2-propanol trap). The gummy residue was dissolved in 200 ml of ice water and neutralized to pH 7 by adding saturated sodium carbonate solution. The solid was collected and recrystallized from N,N-dimethylformamide to afford 15 g of the product as an off-white solid, mp 305° C. (with decomposition).

EXAMPLE 8

N-[4-[4-(2,4-Diamino-6-methyl-5-pyrimidinyl)-1-piperazinyl]benzoyl]glycine, methyl ester A mixture of 3.9 g (0.012 mole) of 4-[4-(2,4-diamino-6-methyl-5-pyrimidinyl)-1-piperazinyl]benzoic acid, 6.5 g (0.039 mole) of diethyl phosphorocyanidate and 6.6 ml (0.047 mole) of triethyl amine in 500 ml of N,N-dimethylformamide (dried over 4H molecular sieves overnight) was stirred at room temperature for five hours. A mixture of 1.8 g (0.014 mole) of glycine methyl ester, hydrochloride, 2 ml (0.014 mole) of triethylamine and 10 ml of N,N-dimethylformamide was added to the suspension and the mixture was stirred at room temperature for another two hours. The solvent was removed under high vacuum (0.1 mm, dry ice-2-propanol trap) at 48° C. The solid residue was dissolved in 200 ml of ice water and neutralized with saturated sodium carbonate solution to pH 8. The solid was collected and washed with 100 ml of water. Recrystallization from acetonitrile gave 2.6 g of the product as a pale yellow solid, mp 255° C. (with decomposition).

EXAMPLE 9

6-Methyl-5-[4-[4-(methylsulfonyl)phenyl]-1-piperazinyl]-2,4-pyrimidinediamine, hydrate (10:2)

A mixture of 7.8 g (0.02 mole) of 6-methyl-5-(1-piperazinyl)-2,4-pyrimidinediamine triacetate, 3.8 g (0.022 mole) of p-fluorophenyl methyl sulfone, 11.70 ml (0.084 mole) of triethylamine and 150 ml of dimethyl sulfoxide was heated under reflux, at 140° C. for 16 hours. The reaction mixture was cooled and poured into 500 ml of ice water. The solid was collected and washed with 100 ml of water. Recrystallization from N,N-dimethylformamide and drying in vacuo at 89° C. for 16 hours gave 1.9 g of the product as a dull solid solvated with 0.2 equivalent of water; mp>310° C.

EXAMPLE 10

5-[4-(4-cyanophenyl)-1-piperazinyl]-6-ethyl-2,4-pyrimidinediamine

A mixture of 2.2 g (0.010 mole) of 6-ethyl-5-(1-piperazinyl)-2,4-pyrimidinediamine, 1.33 g (0.011 mole) of a 4-fluorobenzonitrile and 1.52 g (0.011 mole) of potassium carbonate in 20 ml of dimethyl sulfoxide was heated under reflux at 140° C. for two hours. The reaction mixture was cooled and poured into 100 ml of ice water. The solid was collected and recrystallized from N,N dimethyl formamide to give 2.21 g of the product as a white solid, mp>310° C.

6-Ethyl-5-(1-piperazinyl)-2,4-pyrimidinediamine

A solution of 33.5 g (0.107 mole) of 6-ethyl-5-[4-(phenylmethyl)-1-piperazinyl]-2,4-pyrimidinediamine in 400 ml of acetic acid was hydrogenated over 2 g of 20% palladium on charcoal under 3.5 atmospheres of hydrogen for 23 hours and filtered. The filtrate was concentrated in vacuo to dryness. The solid residue was poured into one liter of 2N sodium hydroxide solution. The solid was collected and washed with 500 ml of water. Recrystallization from acetonitrile and drying in vacuo at 59° C. for 16 hours gave 19.0 g of the product as a white solid; mp 204°–207° C.

6-Ethyl-5-[4-(phenylmethyl)-1-piperazinyl]-2,4-pyrimidinediamine

A mixture of 40.0 g (0.11 mole) of 2,4-dichloro-6-ethyl-5-[4-(phenylmethyl)-1-piperazinyl]-pyrimidine and 200 m of saturated ammonia in ethanol solution was heated at 190° C. in a high pressure stainless steel vessel for 14 hours and cooled. Ethanol was removed and the solid residue was washed first with 200 ml of 1N aqueous sodium hydroxide solution and then with 400 ml of water. Recrystallization from ethanol and drying in vacuo at 55° C. for 16 hours gave 33.8 g of the product as an off-white solid solvated with 0.1 equivalent of water; mp 174°–175° C.

2,4-Dichloro-6-ethyl-5-[4-(phenylmethyl)-1-piperazinyl]-pyrimidine

A mixture of 50.0 g (0.159 mole) of 6-ethyl-5-[4-(phenylmethyl)-1-piperazinyl]-2,4(1H,3H) pyrimidinedione, 26.1 g (0.175 mole) of N,N-diethylaniline and 400 ml of phosphorus oxychloride was heated under reflux for four hours and cooled. Phosphorus oxychloride was removed in vacuo. The oily residue was poured into two liters of ice water, neutralized with saturated aqueous sodium carbonate solution and extracted with ethyl acetate (1.5 liters×2). The organic layer was separated, washed successively with water (two liters) and saturated sodium chloride solution, dried over magnesium sulfate, and concentrated in vacuo to dryness. The oily residue was chilled in the refrigerator for three hours and the solid that formed was collected and washed with 200 ml of petroleum ether to give 39.0 g of the product as a pale yellow solid. It was used in the next reaction without further purification.

6-Ethyl-5-[4-(phenylmethyl)-1-piperazinyl]-2,4(1H,3H)-pyrimidinedione

A mixture of 57.0 g (0.260 mole) of 5-bromo-6-ethyl-2,4(1H,3H)pyrimidinedione and 26.6 g (0.286 mole) of anhydrous potassium fluoride in 176 ml (1 mole) of 1-benzylpiperazine was heated under reflux at 140° C. for four hours and cooled. The reaction mixture was poured into 1000 ml of ice water. The solid was collected and washed with water. Recrystallization from N,N dimethylformamide and drying in vacuo at 59° C. for 16 hours gave the product as an off-white solid; mp 255°–256° C.

EXAMPLE 11

4-[4-(2,4-Diamino-6-ethyl-5-pyrimidinyl)-1-piperazinyl]benzoic acid

A solution of 10.0 g (0.031 mole) of 5-[4-(4-cyanophenyl)-1-piperazinyl]-6-ethyl-2,4-pyrimidinediamine in 150 ml of hydrochloric acid was heated under reflux for four hours. The solution was cooled and poured into 500 ml of ice water. The solid was collected and washed with 100 ml of water. The solid was suspended in 300 ml of ice water and 50% aqueous sodium hydroxide solution was added dropwise until solution occurred. The solution was filtered and the filtrate was acidified with 10% aqueous citric acid to pH 5. The solid was collected and washed with 100 ml of water. Recrystallization from N,N-dimethylformamide and drying in vacuo at 89° C. for 16 hours gave 9.60 g of the product as a white powder, mp>300° C.

EXAMPLE 12

N-[4-[4-(2,4-Diamino-6-ethyl-5-pyrimidinyl)-1-piperazinyl]benzoyl]-L-glutamic acid, diethyl ester A mixture of 4.1 g (0.012 mole) of 4-[4-(2,4-diamino-6-ethyl-5-pyrimidinyl)-1-piperazinyl]-benzoic acid, 6.5 g (0.040 mole) of diethyl phosphorocyanidate and 5.6 ml (0.040 mole) of triethylamine in 500 ml of N,N-dimethylformamide (dried over 4 Å molecular sieves overnight) was stirred at room temperature for two hours. To the resulting clear solution was added a mixture of 3.2 g (0013 mole) of L-diethyl glutamate hydrochloride and 1.8 ml (0013 mole) of triethylamine in 10 ml of N,N-dimethylformamide, and the mixture was stirred at ambient temperature for three hours. The solvent was removed under high vacuum (0.1 mm dry ice-2-propanol trap) at 40° C. The gummy residue was poured into 3.00 ml of ice water and adjusted to pH 8 by adding a saturated sodium carbonate solution. The solid was collected and recrystallized from acetonitrile to give 2.8 g of the product as an off-white powder; mp 226°–228° C.

EXAMPLE 13

N-[4-[4-(2,4-Diamino-6-ethyl-5-pyrimidinyl)-1-piperazinyl]benzoyl]-L-glutamic acid A mixture of 2.0 g (3.85 mmole) of N-[4-[4-(2,4-diamino-6-ethyl-5-pyrimidinyl)-1-piperazinyl]benzoyl]-L-glutamic acid diethyl ester and 0.6 g (7.70 mmole) of a 50% aqueous sodium hydroxide solution in 100 ml of methanol was stirred at room temperature for 16 hours. Methanol was removed in vacuo below 23° C. The residue was dissolved in 50 ml of ice water and filtered. The filtrate was acidified with citric acid to pH 5. The solid precipitate was collected, washed with water, and triturated with boiling ethanol. After drying in vacuo at 67° for 16 hours, 1.3 g of the product was obtained as a white powder; mp 275° C. (with decomposition).

EXAMPLE 14

5-[4-(4-cyanophenyl)-1-piperazinyl]-6-propyl-2,4-pyrimidinediamine

A mixture of 9.6 g (0.0407 mole) of 5-(1-piperazinyl)-6-propyl-2,4-pyrimidinediamine, 5.4 g (0.0448 mole) of 4-fluorobenzonitrile and 6.18 g (0.0448 mole) of sodium carbonate in 200 ml of dimethyl sulfoxide was heated at 140° C. for two hours. The reaction mixture was cooled and poured into 500 ml of ice water. The solid was collected and recrystallized from N,N-dimethylformamide to give 11.7 g of the product as a white solid; mp>300° C.

5-(1-piperazinyl)-6-propyl-2,4-pyrimidinediamine

A solution of 28.6 g (0.088 mole) of 5-[4-phenylmethyl)-1-piperazinyl]-6-propyl-2,4-pyrimidinediamine in 500 ml of acetic acid was hydrogenated over 2 g of 20% palladium on charcoal under 3.5 atmospheres of hydrogen for 18.7 hours and filtered. over 2 g of 20% palladium on charcoal under 3.5 atmospheres of hydrogen for 18.7 hours and filtered. The filtrate was concentrated in vacuo to dryness. The oily residue was poured into one liter of ice water and neutralized with 50% aqueous sodium hydroxide to pH 8. The solid was collected, washed with water (500 ml) and recrystallized from acetonitrile to afford 17.0 g of the product as a white solid; mp 175°–176° C.

5-[4-(phenylmethyl)-1-piperazinyl]-6-propyl-2,4-pyrimidinediamine

A mixture of 70 g of 2,4-dichloro-5-[4-(phenylmethyl)-1-piperazinyl]-6-propyl-pyrimidine (from the previous step, assumed to be 0.159 mole) and 400 ml of a saturated solution of ammonia in ethanol was heated at 185° C. in a stainless steel pressure vessel for 14 hours. The reaction mixture was chilled in an ice bath and the solid was collected and washed with water (200 ml). Recrystallization from acetonitrile and drying in vacuo at 59° C. gave 30.8 g of the product as a white solid; mp 157°–160° C.

2,4-Dichloro-5-[4-(phenylmethyl)-1-piperazinyl]-6-propylpyrimidine

A mixture of 52.5 g (0.159 mole) of 5-[4-(phenylmethyl)-1-piperazinyl]-6-propyl-2,4(1H,3H)pyrimidinedione, 26.1 g (0.175 mole) of N,N diethylaniline and 500 ml of phosphorus oxychloride was heated under reflux for four hours and cooled. Phosphorus oxychloride was removed in vacuo. The oily residue was poured into 1.5 liters of ice water and neutralized with saturated sodium carbonate solution to pH 7. The aqueous mixture was extracted twice with one liter portions of ethyl acetate. The organic layer was separated, washed successively with water (one liter) and saturated sodium chloride solution (400 ml), dried (magnesium sulfate), and concentrated in vacuo to give 70 g of an oily residue. It was used in the next reaction without further purification.

5-[4-(Phenylmethyl)-1-piperazinyl]-6-propyl-2,4(1H,3H)-pyrimidinedione

A mixture of 53.3 g (0.229 mole) of 5-bromo-6-propyl-2,4(1H,3H)pyrimidinedione and 23.7 g (0.252 mole) of anhydrous potassium fluoride in 176 ml (1.0 mole) of 1-benzylpiperazine was heated under reflux at 140° C.

for 14 hours. The reaction mixture was cooled to 80° C. and 100 ml of ethanol was added. The mixture was poured into one liter of ice water. The solid was collected and washed with one liter of water. Recrystallization from ethanol and drying in vacuo at 59° C. for 16 hours gave 44.1 g of the product as an off-white solid; mp 233°–235° C.

5-[4-(Phenylmethyl)-1-piperazinyl]-6-propyl-2,4(1H,3H)-pyrimidinedione

A mixture of 53.3 g (0.229 mole) of 5-bromo-6-propyl-2,4(1H,3H)pyrimidinedione and 23.7 g (0.252 mole) of anhydrous potassium fluoride in 176 ml (1.0 mole) of 1-benzylpiperazine was heated under reflux at 140° C. for 14 hours. The reaction mixture was cooled to 80° C. and 100 ml of ethanol was added. The mixture was poured into one liter of ice water. The solid was collected and washed with one liter of water. Recrystallization from ethanol and drying in vacuo at 59° C. for 16 hours gave 44.1 g of the product as an off-white solid; mp 233°–235° C.

EXAMPLE 15

4-[4-(2,4-Diamino-6-propyl-5-pyrimidinyl)-1-piperazinyl]benzoic acid

A solution of 10.0 g (0.030 mole) of 5-[4-(4-cyanophenyl)-1-piperazinyl]-6-propyl-2,4-pyrimidinediamine in 150 ml of hydrochloric acid was heated under reflux for four hours. The solution was cooled and poured into 500 ml of ice water. The solid was collected and washed with 100 ml of water. The solid was suspended in 300 ml of ice water and 50% sodium hydroxide solution was added dropwise until a clear solution formed. The solution was filtered and the filtrate was acidified with 10% citric acid to pH 5. The solid was collected and washed with 100 ml of water. Recrystallization from N,N-dimethylformamide and drying in vacuo at 89° C. for 16 hours gave 9.57 g of the product as a white powder; mp 285° C. (with decomposition).

EXAMPLE 16

N-[4-[4-(2,4-Diamino-6-propyl-5-pyrimidinyl)-1-piperazinyl]benzoyl]-L-glutamic acid, diethyl ester A mixture of 3.2 g (0.0091 mole) of 4-[4-(2,4-diamino-6-propyl-5-pyrimidinyl]-1-piperazinyl]benzoic acid, 4.9 g (0.030 mole) of diethyl phosphorocyanidate and 4.2 ml (0.030 mole) of triethylamine in 200 ml of of N,N-dimethylformamide (dried over 4 Å molecular sieves overnight) was stirred at room temperature for two hours. To the resulting clear solution was added a mixture of 2.4 g (0.010 mole) of diethyl glutamate hydrochloride and 1.4 ml (0.010 mole) of triethylamine in 10 ml of N,N-dimethylformamide, and the solution was stirred for another hour. The solvent was removed under high vacuum (0.1 mm, dry ice-2-propanol trap) at 40° C. The gummy residue was poured into 100 ml of ice water. The solid was collected and recrystallized from N,N-dimethylformamide to give 1.9 g of the product as an off-white powder; mp 175°–180° C.

EXAMPLE 17

N-[4-[4-(2,4-Diamino-6-propyl-5-pyrimidinyl)-1-piperazinyl]benzoyl]-L-glutamic acid A mixture of 1.3 g (2.47 mmole) of N-[4-[4-(2,4-diamino-6-propyl-5-pyrimidinyl)-1-piperazinyl]-benzoyl]-L-glutamic acid diethyl ester and 0.4 g (4.94 mmole) of a 50% aqueous sodium hydroxide solution in 300 ml of methanol was stirred at room temperature for four hours. One drop of 50% sodium hydroxide solution was added and the reaction mixture became a clear solution. Methanol was removed in vacuo below 23° C. The residue was dissolved in 200 ml of ice water and filtered. The filtrate was acidified with citric acid to pH 6. The precipitate was collected, washed with water, and triturated with boiling ethanol. After drying in vacuo at 78° C. for 16 hours, 0.9 g of the product was obtained as white powder, mp 280°–284° C.

EXAMPLE 18

4-[4-(2,4-Diamino-6-propyl-5-pyrimidinyl)-1-piperazinyl]benzoic acid, ethyl ester A mixture of 1.0 g (2.96 mmole) of 5-[4-(4-cyanophenyl)-1-piperazinyl]-6-propyl-2,4-pyrimidinediamine, 15 ml of 95% ethanol and 15 ml of sulfuric acid was heated under reflux at 100° C. for four hours and cooled. The solution was poured into 200 ml of ice water and filtered. The filtrate was kept cool and neutralized with 50% aqueous sodium hydroxide solution to pH 7. The solid was collected and washed with 50 ml of water. Recrystallization from N,N-dimethylformamide and drying in vacuo at 78° C. for 16 hours gave 0.7 g of the product as a white solid, mp 215°–216° C.

EXAMPLE 19

5-[4-(4-cyanophenyl)-1-piperazinyl]-6-methyl-2,4-pyrimidinediamine

A mixture of 8.0 g (0.023 mole) of 2,4-dichloro-5-[4-(4-cyanophenyl)-1-piperazinyl]-6-methylpyrimidine and 200 ml of a saturated solution of ammonia in ethanol was heated at 190° C. in a stainless steel pressure vessel for 14 hours and cooled. Ethanol was removed in vacuo and the solid residue was washed with 200 ml of water. Recrystallization from N,N-dimethylformamide and drying in vacuo at 78° C. for 16 hours gave 4.8 g of the product as an off-white solid; mp>300° C.

2,4-Dichloro-5-[4-(4-cyanophenyl)-1-piperazinyl]-6-methylpyrimidine

A mixture of 9.0 g (0.029 mole) of 5-[4-(4-cyanophenyl)-1-piperazinyl]-6-methyl-2,4(1H,3H)pyrimidinedione, 4.8 g (0.032 mole) of N,N-diethylaniline and 300 ml of phosphorus oxychloride was heated under reflux for three hours and cooled. Phosphorus oxychloride was removed in vacuo. The oily residue was partitioned between ethyl acetate (500 ml) and 500 ml of cold 5N sodium carbonate solution. The organic layer was separated, washed successively with 500 ml of water and 200 ml of saturated sodium chloride solution, dried over magnesium sulfate, and concentrated in vacuo to dryness. The oily residue was chilled in the refrigerator for 16 hours and the solid that formed was collected and washed with 200 ml of petroleum ether to give the product as a light yellow solid.

5-[4-(4-cyanophenyl)-1-piperazinyl]-6-methyl-2,4-(1H,3H)-pyrimidinedione

A mixture of 20.5 g (0.10 mole) of 5-bromo-6-methyl-2,4(1H,3H)-pyrimidinedione, 18.1 g (0.10 mole) of 4-(4-cyanophenyl)piperazine, 6.4 g (0.11 mole) of anhydrous potassium fluoride, 15.2 g (0.1 mole) of powdered potassium carbonate in 100 ml of hexamethyl phosphoramide was heated at 140° C. for 24 hours. The mixture was cooled and poured into 500 ml of ice water. The solid was collected and washed with 100 ml of water. Recrystallization from N,N-dimethylformamide and drying in vacuo at 78° C. for 16 hours gave 9.3 g of the product as a dull solid.

4-(4-cyanophenyl)piperazine

A mixture of 20.0 g of 4-[1-(4-phenylmethyl)-piperazinyl]benzonitrile in 400 ml of methanol was hydrogenated over 2 g of 20% palladium on charcoal under 3.5 atmospheres of hydrogen for 20 hours and filtered. The filtrate was concentrated in vacuo to dryness. The residue was used in the next reaction without further purification.

4-[1-(4-Phenylmethyl)-piperazinyl]-benzonitrile

A mixture of 17.6 g (0.10 mole) of N-benzylpiperazine, 12.1 g (0.10 mole) of p-fluorobenzonitrile, 13.8 g (0.01 mole) of potassium carbonate in 100 ml of dimethyl sulfoxide was heated at 140° C. for three hours. The reaction mixture was cooled and poured into 500 ml of ice water. The solid was collected and recrystallized from ethanol to give 22.0 g of the product.

EXAMPLE 20

6-Methyl-5-(4-phenyl-1-piperazinyl)-2,4-pyrimidinediamine, hydrochloride (5:1)

The crude 2,4-dichloro-6-methyl-5-(4-phenyl-1-piperazinyl)pyrimidine (2.1 g, 6.5 mmole) was added to 50 ml of a saturated solution of ammonia in ethanol. The resulting mixture was heated in a steel bomb at 180° for 16 hours. Ethanol was removed and the solid residue was washed with 5N aqueous sodium carbonate solution and then with water and filtered. Recrystallization from methanol twice gave 0.87 g of the product as a dull off-white solid, mp 247°–248°.

2,4-Dichloro-6-methyl-5-(4-phenyl-1-piperazinyl)-pyrimidine

A mixture of 5.72 g (0.020 mole) of 6-methyl-5-(4-phenyl-1-piperazinyl)-2,4(1H, 3H)-pyrimidinedione, 5 ml of N,N-dimethylaniline and 30 ml of phosphorous oxychloride was heated at 80° for 16 hours. Excess phosphorous oxychloride was removed in vacuo, and the oily residue was poured into 200 ml of ice water. The solid was collected, washed with water, and dried in vacuo at 62° overnight at give 6.20 g of the product as a cream solid which was used directly in the next reaction without further purification.

6-Methyl-5-(4-phenyl-1-piperazinyl)-2,4(1H, 3H)-pyrimidinedione, hydrate (13:1)

A mixture of 20.5 g (0.10 mole) of 5-bromo-6-methyl-2,4(1H, 3H)-pyrimidinedione and 10.3 g (0.11 mole) of potassium fluoride dihydrate in 150 ml of 1-phenylpiperazine was heated under reflux at 105° for 72 hours and cooled. The reaction mixture was poured into 200 ml of ice water. The solid was collected, washed with water, and recrystallized from methanol to give 7.12 g of the product as a white solid, mp>300° C.

EXAMPLE 21

5-[4-(4-chlorophenyl)-1-piperazinyl]-6-methyl-2,4-pyrimidinediamine

A mixture of 5.40 g (0.0168 mole) of 5-[4-(4-chlorophenyl)-1-piperazinyl]-6-methyl-2,4(1H, 3H)-pyrimidinedione, 5 ml of N,N-dimethylaniline and 100 ml of phosphorous oxychloride was heated under reflux for four hours. Phosphorous oxychloride was removed in vacuo. The oily residue was poured into 200 ml of ice water, neutralized with 50% sodium hydroxide solution to pH 8 and extracted twice with 200 ml portions of ethyl acetate. The extracts were washed first with water and then with saturated sodium chloride solution, dried over magnesium sulfate, and concentrated in vacuo to give 5.80 g of a black oily mixture. This material was dissolved in 30 ml of cold saturated solution of ammonia in ethanol and heated in a steel bomb at 185° C. for 16 hours. The solvent was removed in vacuo and the solid residue was washed with water. Recrystallization of the crude solid from N,N-dimethylformamide and drying at 67° C. overnight afforded 2.95 g of the product as a dull off-white solid, mp 285° dec.

5-[4-(4-Chlorophenyl)-1-piperazinyl]-6-methyl-2,4-(1H, 3H)-pyrimidinedione

A mixture of 20.50 g (0.100 mole) of 5-bromo-6-methyl-2,4(1H, 3H)pyrimidinedione, 26.96 g (0.100 mole of 1-(4-chlorophenyl)-piperazine, 10.35 g (0.110 mole) of potassium fluoride dihydrate and 41.40 g (0.300 mole) of potassium carbonate in 200 ml of dimethylsulfoxide was heated at 80° for 72 hours. The reaction mixture was cooled and poured into 1 l of ice water. The solid was collected, washed with water, and recrystallized from ethanol to give 6.05 g of the product as a dull yellow solid.

EXAMPLE 22

5-[4-(4-aminophenyl-1-piperazinyl]-6-methyl-2,4-pyrimidinediamine

A suspension of 8.0 g (0.024 mole) of 6-methyl-5-[4-(4-nitrophenyl)-1-piperazinyl]-2,4-pyrimidinediamine in 100 ml of acetic acid was hydrogenated over 0.5 g of 5% palladium on charcoal under 3.5 atmospheres of hydrogen for 18 hours and filtered. The filtrate was concentrated in vacuo to dryness. The solid residue was dissolved in 500 ml of ice water and neutralized with ammonium hydroxide to pH 8. The solid was collected and washed with 20 ml of water. Recrystallization from N,N-dimethylformamide and drying in vacuo at 89° C. for 16 hours gave 6.1 g of the product as light brown solid, mp 237°–239° C.

EXAMPLE 23

N-[4-[4-(2,4-Diamino-6-methyl-5-pyrimidinyl)-1-piperazinyl]benzoyl]-glycine

A mixture of 1.5 g (3.76 mmole) of N-[4-[4-(2,4-diamino-6-methyl-5-pyrimidinyl)-1-piperazinyl]benzoylglycine methyl ester and 3.8 ml (3.8 mmole of a 1N aqueous sodium hydroxide solution in 500 ml of methanol was stirred at room temperature for 16 hours. The reaction mixture remained cloudy. A solution of 0.4 ml of 1N sodium hydroxide in 200 ml of methanol was added and the reaction mixture was stirred for another two hours and became clear solution. Methanol was removed in vacuo. The solid residue was dissolved in 200 ml of water and filtered. The filtrate was acidified with citric acid to pH 6. The precipitate was collected, washed with water, and triturated with 200 ml of boiling methanol. After drying in vacuo at 78° C. for 16 hours, 1.30 g of the product was obtained as white powder, mp>310° C.

EXAMPLE 24

4-[4-(2,4-Diamino-6-methyl-5-pyrimidinyl)-1-piperazinyl]-N,N-dimethylbenzenesulfonamide A mixture of 10.4 g (0.05 mole) of 6-methyl-5-(1-piperazinyl)-2,4-pyrimidinediamine triacetate, 10.1 g (0.05 mole) of 4-fluoro-N,N-dimethylbenzenesulfonamide, 6.4 g (0.055 mole) of anhydrous potassium fluoride, and 27.6 g (0.2 mole) of powdered potassium carbonate in 100 ml of dimethylsulfoxide was heated at 120° C. for four hours. The reaction mixture was cooled and poured into 300 ml of ice water. The solid was collected and washed with ml of water. Recystallization from N,N-dimethylformamide gave 6.5 g of the product as an off-white solid, mp 301°–304° C.

4-Fluoro-N,N-dimethylbenzenesulfonamide

A solution of 38.9 g (0.20 mole) of 4-fluorobenzenesulfonylchloride in 20 ml of methylene chloride was added slowly to 300 ml of a 40% aqueous dimethylamine solution during 0.5 hour period. The reaction was exothermic. After the reaction mixture was cooled a yellow solid was precipitated. The solid was collected, dissolved in 300 ml of ethyl acetate, and dried over magnesium sulfate. The solution was concentrated to 100 ml and a light yellow crystal formed. The crystal was collected and air-dried to afford 39 g of the product, mp 40°–43° C.

EXAMPLE 25

6-Methyl-5-[4-[4-(trifluoromethyl)phenyl]-1-piperazinyl]-2,4-pyrimidinediamine A mixture of 1.9 g (5.0 mmole) of 6-methyl-5-(1-piperazinyl)-2,4-pyrimidinediamine triacetate, 0.8 g (5.0 mmole) of 1-fluoro-4-(trifluoromethyl)benzene 0.4 g (6.0 mmole) of anhydrous potassium fluoride and 3.31 g (2.4 mmole) of potassium carbonate in 20 ml of dimethylsulfoxide was heated at 130° C. for 16 hours. The reaction mixture was cooled and poured into 150 ml of ice water. The solid was collected and washed with water. Recrystallization from N,N-dimethylformamide gave 0.4 g of the product as an off-white solid, mp 255°–258° C.

We claim:

1. A compound having the structural formula I

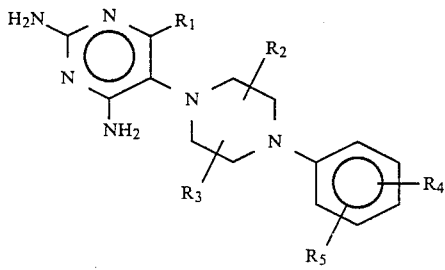

where
- A. $R_1$ is hydrogen or alkyl of from one to six carbon atoms;
- B. $R_2$ and $R_3$ are independently hydrogen or methyl;
- C. $R_4$ and $R_5$ are independently:
  - (1) hydrogen;
  - (2) halogen;
  - (3) nitro;
  - (4) cyano;
  - (5) trifluoromethyl;
  - (6) hydroxyl;
  - (7) alkyl of from one to six carbon atoms;
  - (8) alkoxyl of from one to six carbon atoms;
  - (9) alkanoyl of from one to six carbon atoms;
  - (10) $-NR_6R_7$, where $R_6$ and $R_7$ are independently
    - (a) hydrogen,
    - (b) alkyl of from one to six carbon atoms,
    - (c) alkanoyl of from one to six carbon atoms;
  - (11) $-COOR_8$ where $R_8$ is
    - (a) hydrogen,
    - (b) a pharmaceutically acceptable metal cation,
    - (c) a pharmaceutically acceptable amine cation,
    - (d) alkyl of from one to six carbon atoms;
  - (12) $-CONR_9R_{10}$ where $R_9$ and $R_{10}$ are independently
    - (a) hydrogen,
    - (b) alkyl of from one to six carbon atoms,
    - (c) alkyl of from one to six carbon atoms, substituted with one or two carboxyl groups,
    - (d) alkyl of from one to six carbon atoms, substituted with one to two carboxyl groups and one $-OH$, $-SH$, or $-NH_2$ group,
    - (e) alkyl of from one to six carbon atoms, substituted with one or two carboalkoxy groups of from one to six carbon atoms,
    - (f) alkyl of from one to six carbon atoms, substituted with one or two carboalkoxy groups of from one to six carbon atoms and one $-OH$, $-SH$, or $-NH_2$ group;
  - (13)

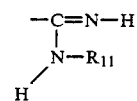

where $R_{11}$ is hydrogen, or alkyl of from one to six carbon atoms; or
  - (14) $-SO_2R_{12}$ where $R_{12}$ is
    - (a) hydroxyl,
    - (b) alkyl of from one to six carbon atoms,
    - (c) alkoxy of from one to six carbon atoms, or
    - (d) $-NHR_{13}$ where $R_{13}$ is hydrogen or alkyl of from one to six carbon atoms;
    and the pharmaceutically acceptable salts thereof.

2. A compound in accordance with claim 1 wherein $R_4$ and $R_5$ are independently
- A. nitro;
- B. cyano;
- C. trifluoromethyl;
- D. alkanoyl of from one to six carbon atoms;
- E. $-COOR_8$ where $R_8$ is
  - (1) hydrogen,
  - (2) a pharmaceutically acceptable metal cation,
  - (3) a pharmaceutically acceptable amine cation, or
  - (4) alkyl of from one to six carbon atoms;
- F. $-CONR_9R_{10}$ where $R_9$ and $R_{10}$ are independently
  - (1) hydrogen,
  - (2) alkyl of from one to six carbon atoms,
  - (3) alkyl of from one to six carbon atoms, substituted with one or two carboxyl groups,
  - (4) alkyl of from one to six carbon atoms, substituted with one or two carboxyl group and one $-OH$, $-SH$, or $-NH_2$ group, (5) alkyl of from one to six carbon atoms, substituted with one or two carboalkoxy groups of from one to six carbon atoms
(6) alkyl of from one to six carbon atoms, substituted with one or two carboalkoxy groups of from one to six carbon atoms and one —OH, —SH, or —NH$_2$ group;

G.

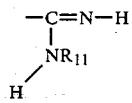

where R$_{11}$ is hydrogen or alkyl of from one to six carbon atoms; or

H. —SO$_2$R$_{12}$ where R$_{12}$ is
(1) hydroxyl,
(2) alkyl of from one to six carbon atoms,
(3) alkoxy of from one to six carbon atoms, or
(4) —NHR$_{13}$ where R$_{13}$ is hydrogen or alkyl of from one to six carbon atoms;
and the pharmaceutically acceptable salts thereof.

3. A compound in accordance with claim 1 wherein R$_4$ and R$_5$ are independently
A. hydrogen;
B. halogen;
C. hydroxyl;
D. alkyl of from one to six carbon atoms;
E. alkoxyl of from one to six carbon atoms; or
F. —NR$_6$R$_7$, where R$_6$ and R$_7$ are independently
(1) hydrogen,
(2) alkyl of from one to six carbon atoms,
(3) alkanoyl of from one to six carbon atoms;
and the pharmaceutically acceptable salts thereof.

4. A compound in accordance with claim 1 having the name 4-[4-(2,4-diamino-6-methyl-5-pyrimidinyl)-1-piperazinyl]benzoic acid and the pharmaceutically acceptable salts thereof.

5. A compound in accordance with claim 1 having the name 4-[4-(2,4-diamino-6-methyl-5-pyrimidinyl)-1-piperazinyl]benzoic acid ethyl ester and the pharmaceutically acceptable salts thereof.

6. A compound in accordance with claim 1 having the name 5-[4-(4-cyanophenyl)-1-piperazinyl]-6-methyl-2,4-pyrimidinediamine and the pharmaceutically acceptable salts thereof.

7. A compound in accordance with claim 1 having the name N-[4-[4-(2,4-diamino-6-methyl-5-pyrimidinyl)-1-piperazinyl]-benzoyl]-L-glutamic acid and the pharmaceutically acceptable salts thereof.

8. A compound in accordance with claim 1 having the name N-[4-[4-(2,4-diamino-6-methyl-5-pyrimidinyl)-1-piperazinyl]-benzoyl]-L-glutamic acid diethyl ester and the pharmaceutically acceptable salts 9. A compound in accordance with claim 1 having the name 6-methyl-5-[4-(4-nitrophenyl)-1-piperazinyl]-2,4-pyrimidinediamine and the pharmaceutically acceptable salts thereof.

10. A compound in accordance with claim 1 having the name 5-[4-(4-acetylphenyl)-1-piperazinyl]-6-methyl-2,4-pyrimidinediamine and the pharmaceutically acceptable salts thereof.

11. A compound in accordance with claim 1 having the name 4-[4-(2,4-diamino-6-methyl-pyrimidinyl)-1-piperazinyl]-N-methyl benzamide and the pharmaceutically acceptable salts thereof.

12. A compound in accordance with claim 1 having the name [4-(2,4-diamino-6-methyl-5-pyrimidinyl)-1-piperazinyl]benzoyl]glycine and the pharmaceutically acceptable salts thereof.

13. A compound in accordance with claim 1 having the name N-[4-[4-(2,4-diamino-6-methyl-5-pyrimidinyl)-1-piperazinyl]benzoyl]glycine methyl ester and the pharmaceutically acceptable salts thereof.

14. A compound in accordance with claim 1 having the name 6-methyl-5-[4-[4-(methylsulfonyl)phenyl]-1-piperazinyl]-2,4-pyrimidinediamine and the pharmaceutically acceptable salts thereof.

15. A compound in accordance with claim 1 having the name 5-[4-(4-cyanophenyl)-1-piperazinyl]-6-ethyl-2,4-pyrimidinediamine and the pharmaceutically acceptable salts thereof.

16. A compound in accordance with claim 1 having the name 4-[4-(2,4-diamino-6-ethyl-5-pyrimidinyl)-1-piperazinyl]benzoic acid and the pharmaceutically acceptable salts thereof.

17. A compound in accordance with claim 1 having the name N-[4-[4-(2,4-diamino-6-ethyl-5-pyrimidinyl)-1-piperazinyl]benzoyl]-L-glutamic acid and the pharmaceutically acceptable salts thereof.

18. A compound in accordance with claim 1 having the name N-[4-[4-(2,4-diamino-6-ethyl-5-pyrimidinyl)-1-piperazinyl]benzoyl]-L-glutamic acid diethyl ester, and the pharmaceutically acceptable salts thereof.

19. A compound in accordance with claim 1 having the name 5-[4-(4-cyanophenyl)-1-piperazinyl]-6-propyl-2,4-pyrimidinediamine and the pharmaceutically acceptable salts thereof.

20. A compound in accordance with claim 1 having the name 4-[4-(2,4-diamino-6-propyl-5-pyrimidinyl)-1-piperazinyl]benzoic acid and the pharmaceutically acceptable salts thereof.

21. A compound in accordance with claim 1 having the name N-[4-[4-(2,4-diamino-6-propyl-5-pyrimidinyl)-1-piperazinyl]benzoyl]-L-glutamic acid and the pharmaceutically acceptable salts thereof.

22. A compound in accordance with claim 1 having the name N-[4-[4-(2,4-diamino-6-propyl-5-pyrimidinyl)-1-piperazinyl]benzoyl]-L-glutamic acid diethyl ester and the pharmaceutically acceptable salts thereof.

23. A compound in accordance with claim 1 having the name 4-[4-(2,4-diamino-6-propyl-5-pyrimidinyl)-1-piperazinyl]benzoic acid ethyl ester and the pharmaceutically acceptable salts thereof.

24. A compound in accordance with claim 1 having the name 6-methyl-5-(4-phenyl-1-piperazinyl)-2,4-pyrimidinediamine, hydrochloride and the pharmaceutically acceptable salts thereof.

25. A compound in accordance with claim 1 having the name 5-[4-(4-chlorophenyl)-1-piperazinyl]-6-methyl-2,4-pyrimidinediamine and the pharmaceutically acceptable salts thereof.

26. A compound in accordance with claim 1 having the name 5-[4-(4-aminophenyl-1-piperazinyl]-6-methyl-2,4-pyrimidinediamine and the pharmaceutically acceptable salts thereof.

27. A compound in accordance with claim 1 having the name N-[4-[4-(2,4-Diamino-6-methyl-5-pyrimidinyl)-1-piperazinyl]benzoyl]-glycine and the pharmaceutically acceptable salts thereof.

28. A compound in accordance with claim 1 having the name 4-[4-(2,4-Diamino-6-methyl-5-pyrimidinyl)-1- piperazinyl]-N,N-dimethylbenzenesulfonamide and the pharmaceutically acceptable salts thereof.

29. A compound in accordance with claim 1 having the name 6-Methyl-5-[4-[4-trifluoromethyl)phenyl]-1-piperazinyl]-2,4-pyrimidinediamine and the pharmaceutically acceptable salts thereof.

30. A compound having structural formula II

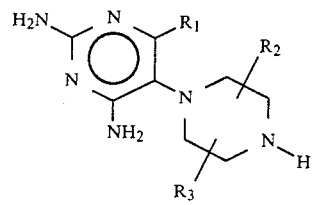

wherein $R_1$ is hydrogen or alkyl of from one to six carbon atoms and wherein $R_2$ and $R_3$ are independently hydrogen or methyl.

31. A pharmaceutical composition comprising an antibacterially effective amount of a compound as defined in claim 1 or a pharmaceutically acceptable salt thereof in combination with a pharmaceutically acceptable carrier.

32. A method for treating bacterial infections in a mammal in need of such treatment by administering an effective amount of a pharmaceutical composition as defined in claim 31.

* * * * *